(12) United States Patent
Chen (10) Patent No.: US 11,130,976 B2
(45) Date of Patent: Sep. 28, 2021

(54) METHOD FOR PREPARING HIGH PRODUCTIVITY MUSHROOM BETA-GLUCAN AND PRODUCTS THEREOF

(71) Applicant: Shiu-Nan Chen, Taipei (TW)

(72) Inventor: Shiu-Nan Chen, Taipei (TW)

(73) Assignee: Shiu-Nan Chen, Taipei (TW)

(*) Notice: Subject to any disclaimer, the term of this patent is extended or adjusted under 35 U.S.C. 154(b) by 127 days.

(21) Appl. No.: 16/257,107

(22) Filed: Jan. 25, 2019

(65) Prior Publication Data
US 2019/0249211 A1 Aug. 15, 2019

(30) Foreign Application Priority Data

Feb. 14, 2018 (TW) ................. 107105531

(51) Int. Cl.
*C12P 19/04* (2006.01)
*C12N 1/14* (2006.01)
*C08B 37/00* (2006.01)
*C12N 13/00* (2006.01)

(52) U.S. Cl.
CPC .......... *C12P 19/04* (2013.01); *C08B 37/0024* (2013.01); *C12N 1/14* (2013.01); *C12N 13/00* (2013.01); *C12N 2500/34* (2013.01)

(58) Field of Classification Search
None
See application file for complete search history.

(56) References Cited

U.S. PATENT DOCUMENTS

| 2008/0160043 A1* | 7/2008 | Kim ........................ A61P 17/00 424/195.15 |
| 2012/0231114 A1* | 9/2012 | Bezerra De Oliveira ................... A21D 2/38 426/18 |

FOREIGN PATENT DOCUMENTS

TW I481718 4/2015

OTHER PUBLICATIONS

Alzorqui (Utrasonics Sonochemistry (2017), vol. 35, pp. 531-540—published online Apr. 26, 2016).*

* cited by examiner

*Primary Examiner* — Susan Hoffman
(74) *Attorney, Agent, or Firm* — Amin, Turocy & Watson, LLP (57) ABSTRACT

A method of preparing a high yield of mushroom β-glucan is provided. The method includes: providing a liquid culture to culture the mushroom mycelium by fermentation, to increase the yields of the mushroom mycelium and polysaccharide, wherein the liquid culture comprises at least two ingredients selected from the groups consisting of glucose, trehalose, a dietary fiber and mannose or derivatives thereof; and rupturing the mushroom mycelium with a continuous multiple-ultrasonic equipment; and removing insoluble matters from the liquid culture. A method of preparing highly pure mushroom β-glucan powder and solution and the products thereof are also provided. By the method of the present disclosure, the yield of mushroom β-glucan is effectively increased, its activity loss is reduced, and the stability of product thereof is improved.

8 Claims, 6 Drawing Sheets

METHOD FOR PREPARING HIGH PRODUCTIVITY MUSHROOM BETA-GLUCAN AND PRODUCTS THEREOF

TECHNICAL FIELD

The present disclosure relates to methods for preparing a novel β-glucan, more particularly, to a method for preparing a mushroom β-glucan with enhanced productivity.

BACKGROUND

Many studies have recently demonstrated that metabolites of mushroom contain quite a number of physiologically active ingredients, including substances like β1-3,1-6 glucan, proteins, triterpenoids, nucleotides, lectins, alkaloids, antibiotics and steroids and the like, which bring about the effects of immunoregulation, anti-inflammation, anti-oxidation, inhibition of platelet coagulation and anti-tumor. Among these, glucan especially has the function of activating immune cells to enhance immunity of an organism, and the use of it in medical applications is therefore of great interest. It should be the tendency of future treatment of cancer that β-glucan is administrated in a manner such as subcutaneous, intraperitoneal and intravenous injection in combination with an anti-cancer drug.

In the preparation method of the a current commercially available glucan product, glucose is used as a common carbon source of a liquid culture, the mushroom mycelium is removed after fermentation, and only the liquid culture containing glucan is allowed to undergo the subsequent treatment. Therefore, the product has a relative low level of glucan, and glycoproteins (remarkable effects of which on various physiological functions such as thrombolysis have been proven) in the mushroom mycelium cannot be applied effectively. Because of the high cost for extraction, easy loss of glucan activity during the process, and the extremely high cost for drying, most of the products are in liquid forms. There still lacks an impeccable method for solving these problems.

TW 481718 has further disclosed that the use of trehalose and mannose in fermentation of mushroom mycelium can produce trehalose-mannose complex polysaccharides having the effect of immunological enhancement. However, in the cited patent TW 481718, a satisfactory degree of homogenization of the mycelium cell rupturing technique cannot be achieved, thus the small molecular ecologies, glycoproteins, polysaccharides or other functional molecules in the mushroom mycelium cannot be used effectively.

In view of the foregoing, it is necessary to propose a method for preparing mushroom β-glucan with high productivity and low activity loss to solve the problems existent in conventional techniques.

SUMMARY

In order to solve the problems described above, the present disclosure provides a novel method for preparing a high yield of mushroom β-glucan, which includes: culturing mushroom mycelium in a liquid culture to increase the yields of the mushroom mycelium and β-glucan, wherein the liquid culture comprises at least two ingredients selected from the group consisting of glucose, trehalose, dietary fiber, and mannose or derivatives thereof; rupturing the mushroom mycelium in the liquid culture with a continuous multiple-ultrasonic equipment; and removing insoluble matters from the liquid culture.

The present disclosure further provides a method for preparing mushroom β-glucan powder with high purity, which includes: adding an excipient to the mushroom β-glucan prepared by the method described above to form a composite, and drying the composite.

The present disclosure further provides mushroom β-glucan powder which includes 20-85 wt % of the mushroom β-glucan.

The present disclosure further provides a method for preparing a highly pure mushroom β-glucan solution, which includes: extracting the mushroom β-glucan prepared by the preparation method described above by filtering or centrifuging to form a mixed liquid; precipitating the mushroom β-glucan in the mixed solution with ethanol; drying the precipitated mushroom β-glucan; and re-dissolving the mushroom β-glucan with distilled deionized water to form an aqueous solution containing the mushroom β-glucan.

The present disclosure further provides a mushroom β-glucan solution at a high concentration, which includes 2-10 mg/mL of the mushroom β-glucan.

By the preparation method of the present disclosure, productivity of glucan can be increased effectively, loss in activity of the mushroom β-glucan can be reduced, and stability of a product of the mushroom β-glucan can be improved.

BRIEF DESCRIPTION OF THE DRAWINGS

The detailed description of the present disclosure is referred to the appended exemplary figures.

DETAILED DESCRIPTION OF THE EMBODIMENTS

The detailed description of the present disclosure will be provided in conjunction with the following embodiments, and any one skilled in the art can readily understand the advantages and effects of the present disclosure based on the content of the present specification. The present disclosure can also be performed or applied by other different modes, and different modifications and alternations can be done on various details of the present specification based on different views and applications without departing from the spirits of the present disclosure. Additionally, all of the ranges and values herein are inclusive and combinable. Any value or point fallen within the range stated herein, for example, any integer, can serve as the minimum or maximum value to derive a sub-range and the like.

According to the present disclosure, a method for preparing a high yield of mushroom β-glucan includes: culturing mushroom mycelium in a liquid culture to increase the yield of mushroom mycelium and concentration of mushroom β-glucan, wherein the liquid culture includes at least two ingredients selected from the group consisting of glucose, trehalose, dietary fiber, and mannose or derivatives thereof; rupturing the mushroom mycelium in the liquid culture with a continuous multiple-ultrasonic equipment; and removing insoluble matters from the liquid culture.

The mushroom β-glucan comprises a compound having the structure of Formula (I):

(I)

wherein the compound includes glucoses as the basic units, and is constituted by linking the basic units through β1-3 glycosidic bonds to form a main chain and through β1-6 glycosidic bonds to form side chains.

The mushroom of the mushroom mycelium is one selected from the group consisting of *Schizophyllum commue, Agarics blaze, Cordyceps sinensis, Ganoderma lucidum, Coriolus versicolor, Anthodia camphorate, Phellinus linteus, Pleuritus citrinopileatus, Lentinula edodes, Hericium erinaceus, Auricularia auricular* and *Flammulina velutipes*.

The liquid culture of the present disclosure includes a carbon source and a nitrogen source, and optionally added microelements, inorganic salts and other growth factor additives.

The carbon source of the liquid culture includes at least two ingredients selected from the group consisting of glucose, trehalose, dietary fiber, and mannose or derivatives thereof. In addition, the carbon source may further include at least one selected from the group consisting of lactose, sucrose, macromolecular fructooligosaccharide, xylose, fucose, galactose, acetylglucosamine, acetylgalactosamine and acetylneuraminic acid, all of which can regulate the yield of β-glucan.

The weight ratio of the carbon source to the nitrogen source of the liquid culture also determines growing status of the mycelium. The presence of a nitrogen source can promote the growth of mycelium, and influence the contents of proteins and lipids in the mycelium. In one embodiment, the nitrogen source of liquid culture is at least one selected from the group consisting of soybean peptone, beef peptone and yeast extract.

The microelement is at least one selected from the group consisting of vitamin A, vitamin B1, vitamin B2, vitamin B12, vitamin C, vitamin D, folic acid, calcium, magnesium, phosphorus and iron, and is employed to accelerate the growth rate of mushroom and to increase the yield of β-glucan.

Trehalose is a qualified substance approved by U.S. Food and Drug Administration (FDA), and has advantages of being organism-protective, anti-freezing, anti-aging, neuro-protective. Trehalose can serves as a stabilizer of biologically active substances, and is used commonly in foods, cosmetics and medicines. Also, the use of trehalose in the liquid culture can increase the yield of secretory and metabolic products of the mushroom. In addition, trehalose cannot be readily subjected to acidolysis or hydrolysis, either, which makes the glucan polymer more stable. Therefore, the glucan prepared by the preparation method according to the present disclosure also has the advantage of extended period of storage.

Mannose is an anti-inflammatory substance, which brings about the effects of activating macrophages, anti-inflammation and regenerating tissues and can stimulate fibroblasts to accelerate wound healing. TW 481718 also discloses that the use of mannose and trehalose in the culturing of mushroom mycelium can increase the yield of mushroom β-glucan, and eating a product thereof can improve the phagocytic activity of phagocytes.

In one embodiment, the use of trehalose, mannose and glucose as the carbon sources of the liquid culture not only can enhance the productivity of β-glucan, but also increase the concentration of other functional molecules such as glycoproteins, small molecular peptides, and the like.

The derivatives of mannose include mannitol, which is also one in the World Health Organization (WHO) essential medicines list for injective drugs used in treatment and prophylaxis of diseases. Since mannitol in mushroom can regulate change in osmotic pressure of the mushroom cells in a fermenting environment and accelerate growth of mushroom cells, the use of mannitol in place of mannose in culturing of mushroom mycelium can also increase yield of mushroom β-glucan and improve effects of the glucan.

Figure 1A:
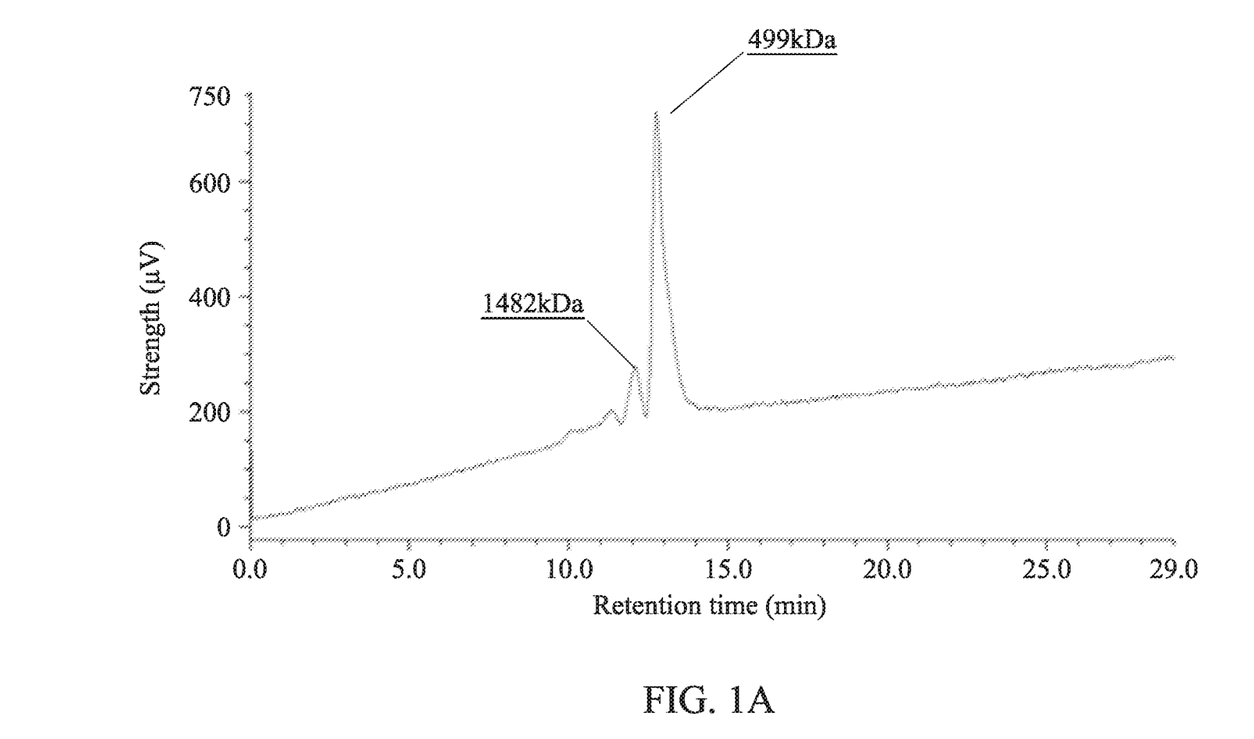
FIG. 1A is a chromatogram showing the result of a high performance liquid chromatography (HPLC) analysis on the mushroom β-glucan obtained from *Ganoderma lucidum* cultured with glucose.
Figure 1B:
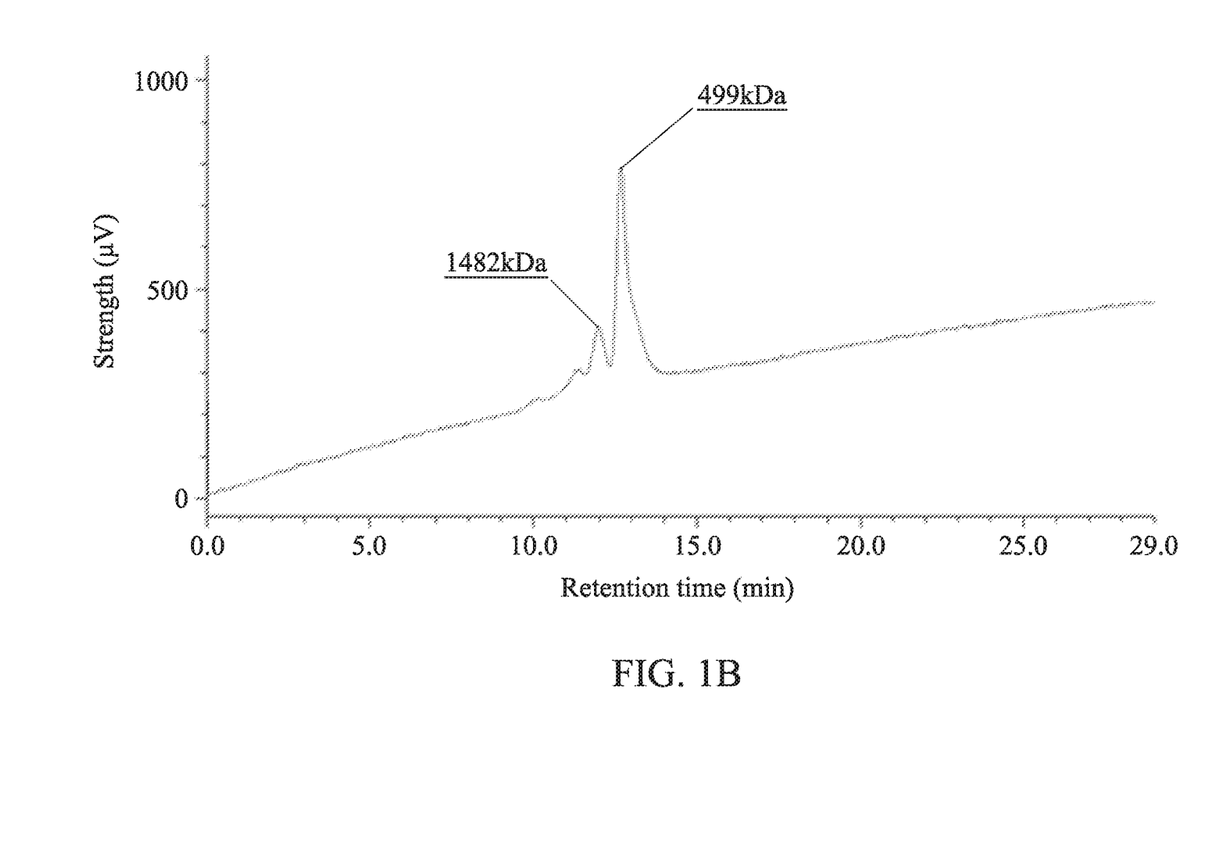
FIG. 1B is a chromatogram showing the result of a high performance liquid chromatography (HPLC) analysis on the mushroom β-glucan obtained from *Ganoderma lucidum* cultured in a liquid culture, wherein the liquid culture includes Fibersol-2, trehalose, mannose and glucose at a weight ratio of 1:1:1:1.
Figure 1C:
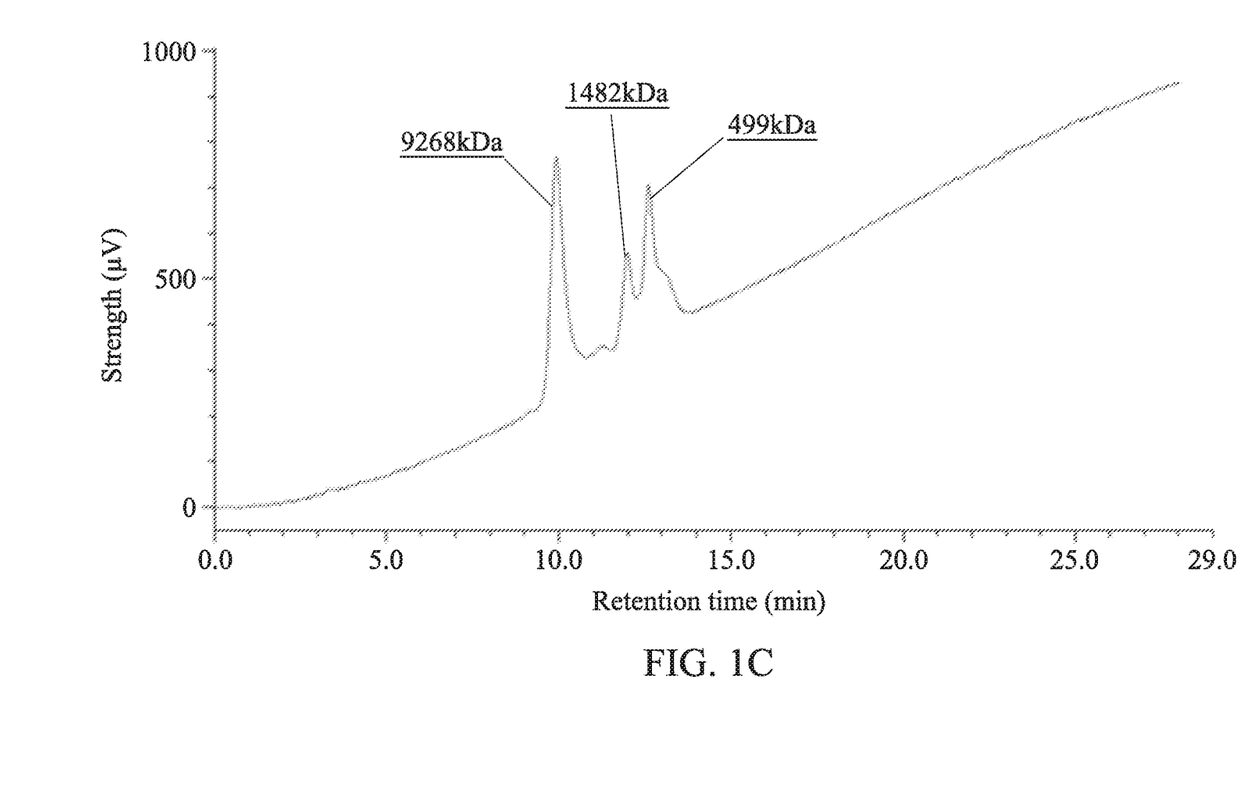
FIG. 1C is a chromatogram showing the result of a high performance liquid chromatography (HPLC) analysis on the mushroom β-glucan obtained from *Schizophyllum commue* cultured in a liquid culture, wherein the liquid culture includes Fibersol-2, trehalose, mannose and glucose at a weight ratio of 1:1:1:1.

The dietary fiber is water-soluble, and includes pectin, gum, viscous matters, vegetable gums, seaweed gel, oligosaccharide or dextrin, wherein the dextrin is preferably maltodextrin (Fibersol-2, also called "indigestible dextrin"), which is a substance approved by FDA and having the properties including difficulty of retrogradation, high stability in an aqueous solution and resistance to freezing storage. Uses in the liquid culture of mushroom are performed, with reference to FIGS. 1A-1C (which represent results of high performance liquid chromatography (HPLC) analysis on mushroom β-glucan obtained by culturing different mushroom species in different liquid cultures), wherein FIG. 1A shows the mushroom β-glucan obtained by culturing *Ganoderma lucidum* in a liquid culture containing glucose, and FIGS. 1B and 1C show the mushroom β-glucan obtained by incubating *Ganoderma lucidum* and *Schizophyllum commue*, respectively, in a liquid culture comprising Fibersol-2, trehalose, mannose and glucose at a weight ratio of 1:1:1:1. As seen from FIGS. 1A and 1B, the addition of Fibersol-2, trehalose and mannose doesn't influence the composition of the mushroom β-glucan obtained from the incubated *Gano-*

*derma lucidum*. However, as can be seen from the change in strength, the significant increase in the yield of mushroom β-glucan results from that Fibersol-2 can promote the conversion of mushroom into mushroom polysaccharide.

In one embodiment, the carbon source in the liquid culture of the present disclosure includes glucose, trehalose and mannose at a weight ratio of 5:1:1 to 1:1:1, preferably at a weight ratio of 1:1:1. The yield of mushroom β-glucan can be increased when such liquid culture is used for culturing the mycelium of *Ganoderma lucidum*, *Schizophyllum commue* or *Antrodia cinnamomea*.

In the most preferred embodiment, the liquid culture of the present disclosure includes glucose, trehalose and mannitol at a weight ratio of 5:1:1 to 1:1:1, preferably at a weight ratio of 1:1:1. In the culturing of the mycelium of *Ganoderma lucidum*, *Schizophyllum commue* or *Antrodia cinnamomea*, the yield of glucan obtained by using such liquid culture is significantly increased in comparison to that obtained by using glucose alone in the culture medium.

In another embodiment, the carbon source of the liquid culture of the present disclosure includes Fibersol-2, glucose, trehalose and mannose at a weight ratio of 1:1:1:1 to 1:10:10:10, and can increase yield of mushroom β-glucan significantly and improve the effect of mushroom β-glucan on immunoregulation when it is used for culturing the mycelium of one selected from the group consisting of *Schizophyllum commue*, *Flammulina velutipes*, *Cordyceps sinensis*, *Lentinula edodes* and *Coriolus versicolor*.

In one embodiment, the carbon source of the liquid culture of the present disclosure includes Fibersol-2, glucose, trehalose and mannose at a weight ratio of 1:1:1:1 to 1:5:5:5, and significant increase in the yield of the mushroom β-glucan can be observed when the carbon source is used for culturing the mycelium of *Schizophyllum commue*, *Flammulina velutipes*, *Cordyceps sinensis*, *Lentinula edodes* or *Coriolus versicolor*.

In the most preferred embodiment, the carbon source of the liquid culture of the present disclosure includes Fibersol-2, glucose, trehalose and mannose at a weight ratio of 1:1:1:1, and a significant increase in yield of the mushroom β-glucan can be observed when the carbon source is used for incubating mycelium of *Schizophyllum commue*.

Differing from the traditional ultrasonic cell breakage techniques, the continuous multiple-ultrasonic rupturing technique utilizes a multiple points ultrasonic generator arrangement and sonic reflection suppression techniques, and uses a series of a plurality of continuous rupturing tanks operated at different ultrasonic frequencies, to rupture the mushroom mycelium cells effectively and completely, and thereby increasing the content of sequent active ingredients, and solving the interference problems of the traditional cell breakage techniques due to the limit of single point ultrasonic generators and standing wave or reflection of different phases.

In order to avoid deterioration of the active ingredients during the rupturing step, compressors or refrigeration chips are arranged in the multiple ultrasonic rupturing tanks to perform the rupturing step in a low temperature environment, and a thermal insulation material containing glass fibers and high hardness foam is employed to achieve the effect of cold insulation and absorb the ultrasonic wave in the rupturing tanks, so as to reduce interference among the tanks, enhance efficiency of the continuous ultrasonic breakage, and have an important influence on the performance and concentration of the sequent product.

In one embodiment, the continuous multiple-ultrasonic rupturing step is carried out at a temperature of 2-18° C.

In one embodiment, the continuous multiple-ultrasonic equipment is operated at a frequency in the range of 20-70 kHz.

Figure 2:
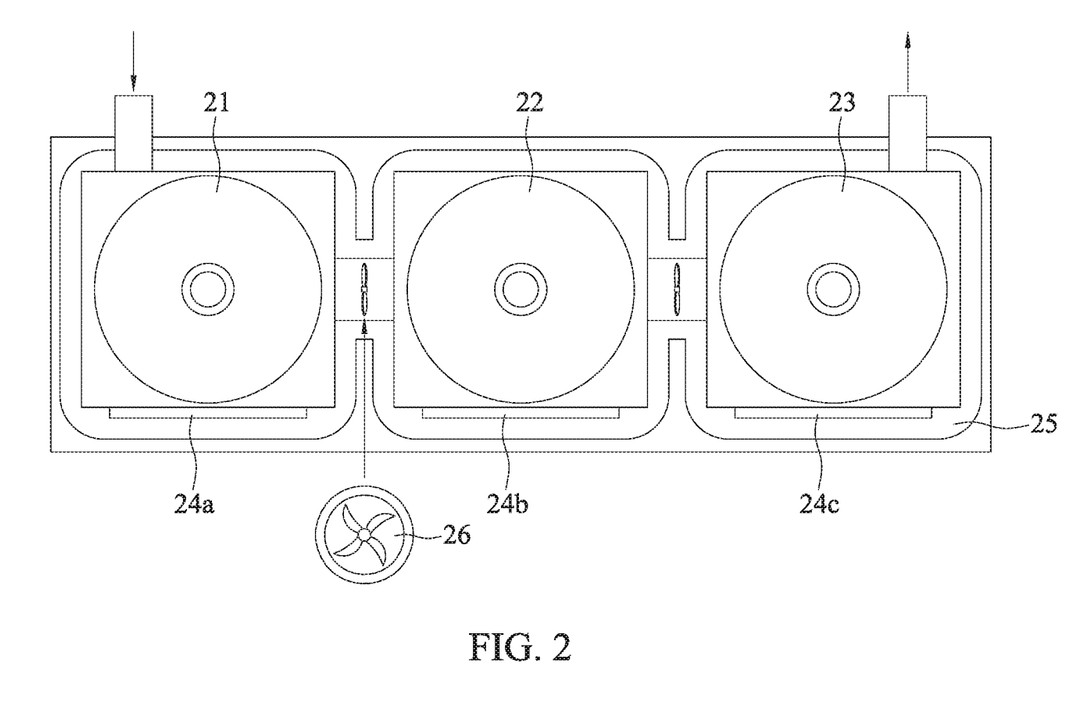
FIG. 2 is a schematic diagram of a continuous multiple-ultrasonic equipment for rupturing cells.

In another embodiment, as shown in FIG. 2, the continuous multiple-ultrasonic cell rupturing equipment has three rupturing tanks 21, 22 and 23, which are operated at ultrasonic frequencies set at 20-30 kHz, 35-45 kHz and 55-65 kHz, respectively; refrigeration chips 24a, 24b and 24c are arranged at the bottom of the tanks to keep the temperature in the tanks at 4° C.; a layer of a thermal insulation material 25 is coated on the refrigeration chips and outside the tanks to achieve the effect of cold insulation and absorb ultrasonic wave of the rupturing tanks; and a high speed grinding blade 26 is arranged on the connection pathway between every two adjacent tanks to assist the breakage of mushroom mycelium.

In the most preferred embodiment, the three rupturing tanks arranged in series are operated at ultrasonic frequencies of 25 kHz, 40 kHz and 60 kHz, respectively.

By using the low temperature continuous multiple-ultrasonic cell rupturing equipment described above, cells of mushroom mycelium can be ruptured completely to allow the small molecular peptides, glycoproteins, polysaccharides or other functional molecules inside mushroom mycelium to be used effectively, and thereby improving effects of the products thereof and enhance feasibility for developing other products in the future.

The step of removing insoluble matters includes, but not limited to, filtering or centrifuging, to remove cell residuals or other water-insoluble matters. Thereafter, the crude product of mushroom β-glucan is stored in a refrigerated environment (at a temperature of 4° C. or less).

The present disclosure further provides a method for preparing highly pure mushroom β-glucan powder, which includes: adding an excipient to the mushroom β-glucan prepared by the preparation method described above to form a composite; and drying the composite.

The drying step includes drying the composite by spray drying or freeze drying.

The excipient includes lactose, sucrose, glucose, fructooligosaccharide, starch or starch derivatives, and dietary fiber. In one embodiment, the excipient is dietary fiber. In another embodiment, the dietary fiber includes dextrin, wherein the dextrin is preferably Fibersol-2. Since Fibersol-2 has high solubility and a high capability to adsorb polysaccharides, the concentration of mushroom β-glucan in a product of mushroom β-glucan powder can be increased by drying, especially the product of mushroom β-glucan powder after subjecting to the spray drying treatment contains water in an amount less than 5.0%, which meets the current requirement for powdery raw materials in most food industries.

In one embodiment, the weight ratio of the mushroom β-glucan to the excipient is 3:1 to 1:8.

In another embodiment, the weight ratio of the mushroom β-glucan to Fibersol-2 is 1:5 to 2:1.

The excipient is water-soluble, and the mushroom β-glucan of the present disclosure can also be dissolved in water well, thus the highly pure mushroom β-glucan powder prepared also has good water solubility.

The present disclosure further provides a mushroom β-glucan powder which includes 20-85 wt % of the mushroom β-glucan.

In one embodiment, the mushroom β-glucan powder prepared by freeze drying and using lactose as the excipient comprises mushroom β-glucan in an amount of 20-40 wt %.

In another embodiment, the mushroom β-glucan powder prepared by spray drying and using Fibersol-2 as the excipient includes mushroom β-glucan in an amount of 70-85 wt %.

The present disclosure further provides a method for preparing a solution of highly pure mushroom β-glucan, which includes: extracting the mushroom β-glucan prepared by the preparation method described above by filtering or centrifuging to obtain a mixed liquid; precipitating the mushroom β-glucan in the mixed liquid with ethanol; drying the precipitated mushroom β-glucan; and re-dissolving the mushroom β-glucan in distilled deionized water to form an aqueous solution of the mushroom β-glucan.

The precipitation step by using ethanol is an effective and low cost extraction technique which can also avoid the risk of residual chemicals due to chemical extraction. In one embodiment, in the precipitation step, the weight ratio of ethanol to the mixed liquid is 1:1, wherein ethanol is preferably anhydrous ethanol containing absolute ethanol in an amount of 99.5% or higher.

The step for drying the precipitates is performed to avoid the risk of residual ethanol in the solution product of mushroom β-glucan. In one embodiment, the drying is carried out at a temperature of 80° C. for 1 hour.

The method for preparing highly pure mushroom β-glucan solution further includes re-dissolving, sterilizing at 121° C. for 20 minutes, and storing the mushroom β-glucan solution at room temperature.

In one embodiment, the method for preparing high purity mushroom β-glucan solution further comprises re-dissolving and thermally sterilizing the aqueous solution, and packaging and storing in a sterilized environment.

In another embodiment, the aqueous solution after thermal sterilization can be filtrated by using a 0.22 μm sterilization filtration membrane.

The filtrated mushroom β-glucan solution after bottling in a sterilized environment is suggested to be stored at a temperature of 4° C.

The present disclosure further provides a mushroom β-glucan solution which includes 2-10 mg/mL of the mushroom β-glucan.

By the preparation method of the present disclosure, the yield of the glucan can be increased effectively, activity loss of the mushroom β-glucan can be reduced, and stability of the product of the mushroom β-glucan can be improved.

The present disclosure will be explained in detail by the following Examples.

Examples 1-6: Experiments of the Effect of Composition of the Liquid Culture on the Yield of the β-Glucan One liter of a liquid culture was formulated in a fermentation container by using sterilized water as solvent, using trehalose, mannose and glucose at a weight ratio of 1:1:1 as carbon source of the liquid culture, and using 0.5 wt % of yeast extract as nitrogen source of the liquid culture. Thereafter, the formulated liquid culture, together with the fermentation container, was placed in an autoclave sterilizer for autoclave sterilization at 121° C. for 15 minutes, and thereafter, was allowed to cool at room temperature. Then, *Ganoderma lucidum* mycelium was added into the liquid culture, and the mushroom mycelium was allowed to generate a large amount of mushroom β-glucan in the liquid culture after being cultured at 30-100 rpm for about 15 days.

The liquid culture containing mushroom mycelium after culturing was treated with the continuous multiple-ultrasonic shown in FIG. 2 to break the mushroom mycelium, wherein the rupturing tanks were each operated at ultrasonic frequencies set at 25 kHz, 40 kHz and 60 kHz, respectively; and insoluble matters were removed by centrifugation. After precipitation with ethanol, freeze drying was performed to give mushroom β-glucan. By using the mushroom β-glucan, influences of compositions of the liquid culture on the yields of the mushroom β-glucan were evaluated, as shown in Table 1.

The treatment methods in Examples 2-3 were the same as that in Example 1; however, the species of mushroom were changed to *Schizophyllum commue* and *Antrodia cinnamomea*, as shown in Table 1. Effects of compositions of the liquid culture on the yields of mushroom β-glucan were evaluated.

The treatment method in Example 4 was the same as that in Example 1. However, mannitol was used in the liquid culture instead of mannose, as shown in Table 1. Effects of compositions of the liquid culture on the yields of mushroom β-glucan are evaluated.

The treatment methods in Examples 5-6 were the same as that in Example 4. However, the species of mushroom were changed to *Schizophyllum commue* and *Antrodia cinnamomea*, as shown in Table 1. Effects of compositions of the liquid culture on the yields of mushroom β-glucan are evaluated.

Comparative Examples 1-3

The treatment methods in Comparative Example 1-3 were the same as that in Example 1. However, glucose alone was used as the carbon source of the liquid culture, and mushroom species are shown in Table 1. Effects of compositions of the liquid culture on the yields of the mushroom β-glucan were evaluated.

TABLE 1

|  | Carbon source of the liquid culture | | Species of the mushroom | Yield of the mushroom β-glucan (g) |
|---|---|---|---|---|
|  | Species | Weight ratio | | |
| Example 1 | trehalose, mannose, glucose | 1:1:1 | *Ganoderma lucidum* | 0.458 |
| Example 2 |  |  | *Schizophyllum commue* | 2.233 |
| Example 3 |  |  | *Antrodia cinnamomea* | 0.021 |
| Example 4 | trehalose, mannitol, glucose | 1:1:1 | *Ganoderma lucidum* | 0.432 |
| Example 5 |  |  | *Schizophyllum commue* | 2.148 |
| Example 6 |  |  | *Antrodia cinnamomea* | 0.018 |
| Comparative Example 1 | glucose | — | *Ganoderma lucidum* | 0.415 |
| Comparative Example 2 |  |  | *Schizophyllum commue* | 1.824 |
| Comparative Example 3 |  |  | *Antrodia cinnamomea* | 0.015 |

As shown in Table 1, by using glucose in combination with trehalose and mannose as the composition of the liquid culture, the yield of glucan from different species of mushroom can be substantially increased by 10-40% than that obtained by using glucose alone, and a similar result is observed when mannitol is used in place of mannose.

Examples 7-15: Experiments of the Effect of Composition of the Liquid Culture on the Yield of the β-Glucan The treatment methods of Examples 7-15 were the same as that in Example 1. However, alterations on compositions of the carbon source in the liquid culture, the ratio of ingredients in the carbon source and the species of mushroom were made as shown in Table 2, wherein the Fibersol-2® (also called "indigestible dextrin") was purchased from Matsutani Chemical Industry Co., Ltd. Effects of compositions of the liquid culture of yields of the mushroom β-glucan are shown in Table 2.

TABLE 2

| | Carbon source of the liquid culture | | Species of the mushroom | Yield of the mushroom β-glucan (g) |
|---|---|---|---|---|
| | Species | Weight ratio | | |
| Example 7 | Fibersol-2, glucose | 1:1 | Ganoderma lucidum | 0.531 |
| Example 8 | | | Schizophyllum commue | 3.175 |
| Example 9 | | | Antrodia cinnamomea | 0.021 |
| Example 10 | Fibersol-2, trehalose, mannose, glucose | 1:1:1:1 | Ganoderma lucidum | 0.854 |
| Example 11 | | | Schizophyllum commue | 4.832 |
| Example 12 | | | Antrodia cinnamomea | 0.033 |
| Example 13 | Fibersol-2, trehalose, mannose, glucose | 1:5:5:5 | Ganoderma lucidum | 0.629 |
| Example 14 | | | Schizophyllum commue | 3.817 |
| Example 15 | | | Antrodia cinnamomea | 0.027 |
| Comparative Example 1 | glucose | — | Ganoderma lucidum | 0.415 |
| Comparative Example 2 | | | Schizophyllum commue | 1.824 |
| Comparative Example 3 | | | Antrodia cinnamomea | 0.015 |

As shown in Table 2, by further combining Fibersol-2 in the composition of the liquid culture, the yield of the mushroom glucan can be substantially increased by 80-160%, such that its production cost is effectively reduced. The high content of mushroom glucan is also beneficial to the sequent product treatment and properties of the final product.

Examples 16-24: Experiments of the Effect of Composition of the Liquid Culture on the Yield of the β-Glucan The treatment methods in Examples 16-24 were the same as that in Example 13, and the changes to the species of mushroom are shown in Table 3. Evaluations on the composition of liquid culture on the yield of mushroom β-glucan were performed, and the results are shown.

Comparative Examples 4-12

The treatment methods in Comparative Examples 4-12 were the same as that in Comparative Example 1, and the changes to the species of mushroom are shown in Table 3. Evaluations of the composition of liquid culture on the productivity of mushroom β-glucan are performed and the results are shown.

TABLE 3

| | Carbon source of the liquid culture | | Species of the mushroom | Yield of the mushroom β-glucan (g) |
|---|---|---|---|---|
| | Species | Weight ratio | | |
| Example 16 | Fibersol-2, trehalose, mannose, glucose | 1:5:5:5 | Agarics blaze | 0.53 |
| Example 17 | | | Cordyceps sinensis | 0.49 |
| Example 18 | | | Phellinus linteus | 0.32 |
| Example 19 | | | Pleuritus citrinopileatus | 0.56 |
| Example 20 | | | Lentinula edodes | 0.47 |
| Example 21 | | | Coriolus versicolor | 0.49 |
| Example 22 | | | Hericium erinaceus | 0.48 |
| Example 23 | | | Auricularia auricula | 0.69 |
| Example 24 | | | Flammulina velutipes | 0.12 |
| Comparative Example 4 | glucose | — | Agarics blaze | 0.42 |
| Comparative Example 5 | | | Cordyceps sinensis | 0.31 |
| Comparative Example 6 | | | Phellinus linteus | 0.27 |
| Comparative Example 7 | | | Pleuritus citrinopileatus | 0.46 |
| Comparative Example 8 | | | Lentinula edodes | 0.31 |
| Comparative Example 9 | | | Coriolus versicolor | 0.33 |
| Comparative Example 10 | | | Hericium erinaceus | 0.38 |
| Comparative Example 11 | | | Auricularia auricula | 0.62 |
| Comparative Example 12 | | | Flammulina velutipes | 0.07 |

As seen in Tables 2 and 3, the preparation methods according to the present disclosure can all increase the yield of mushroom β-glucan significantly when it is used for various species of mushroom, including *Ganoderma lucidum, Schizophyllum commue, Antrodia cinnamomea, Agarics blaze, Cordyceps sinensis, Coriolus versicolor, Phellinus linteus, Pleuritus citrinopileatus, Lentinula edodes, Hericium erinaceus, Auricularia auricula* and *Flammulina velutipes* and the like.

Test Example 1: Test on Ability of Phagocytes

Figure 3:
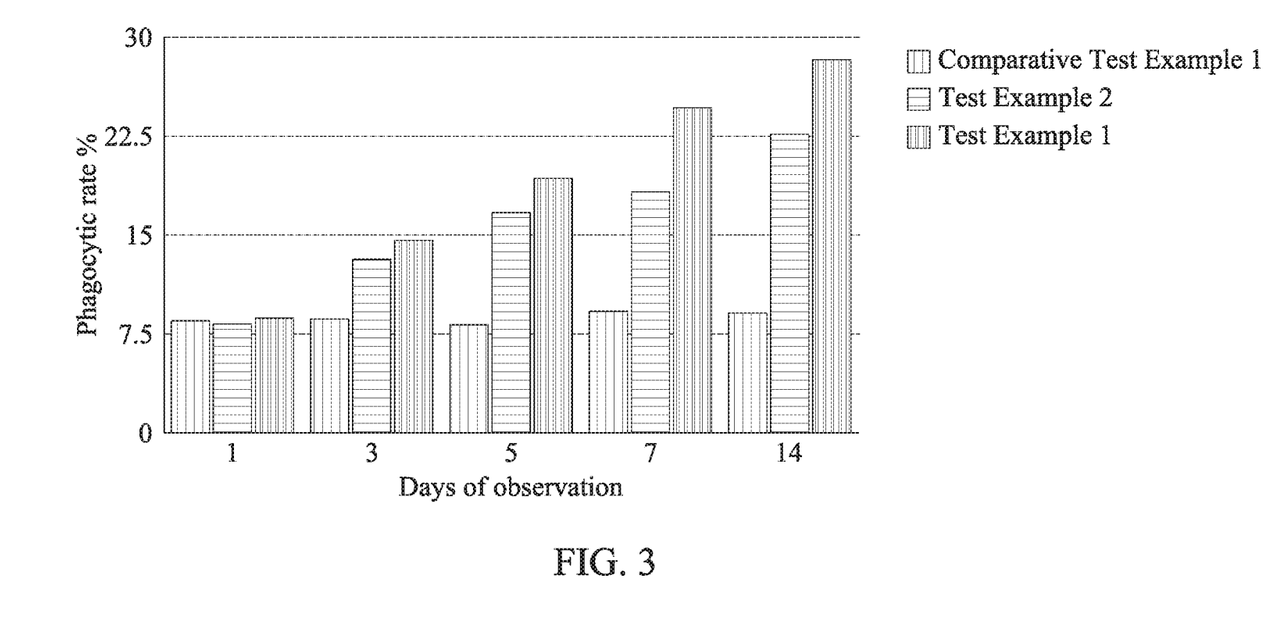
FIG. 3 is a comparative graph showing the change in phagocytosis of mouse phagocytes caused by mushroom β-glucan prepared by different preparation methods according to an embodiment of the present disclosure.

Tests were performed on 15 mice. The mushroom β-glucan of above Example 10 is re-dissolved in distilled deionized water to form a 60 mg/mL aqueous solution of mushroom β-glucan, the mushroom β-glucan solution was fed to mice at a dose of 0.5 mL/day, equaling to each mouse uptaking about 30 mg of mushroom β-glucan per day. One milliliter of blood was drawn from the mice on days 1, 3, 5, 7 and 14 respectively, phagocytes were isolated and their phagocytosis were evaluated with fluorescent microspheres, number of cells having phagocytosis per 100 cells is calculated, and the results are shown in FIG. 3.

Test Example 2: Test on Ability of Phagocytes

The treatment method in Experimental Example 2 was the same as that in Experimental Example 1. However, mushroom β-glucan obtained from direct ethanol extraction in place of that prepared by ultrasonic rupturing was used for evaluating its effect on phagocytosis of mice phagocytes, and the results are shown in FIG. 3.

Comparative Experimental Example 1: Test on Ability of Phagocytes

The treatment method in Comparative Experimental Example 1 is the same as that in Experimental Example 1, however, physiological saline is used in place of mushroom β-glucan solution for feeding mice, their effects on phagocytosis of mice phagocytes are evaluated, and the results are shown in FIG. 3.

As seen in FIG. 3, the phagocytosis of phagocytes in mice fed with mushroom β-glucan prepared by ultrasonic breakage are higher than those in Comparative Experimental Example 1, and the phagocytosis of phagocytes in mice fed with mushroom β-glucan prepared by ultrasonic breakage are better than those in mice fed with the mushroom β-glucan extracted with ethanol.

Test Example 3: Test on Ability of Natural Killer Cells

Figure 4:
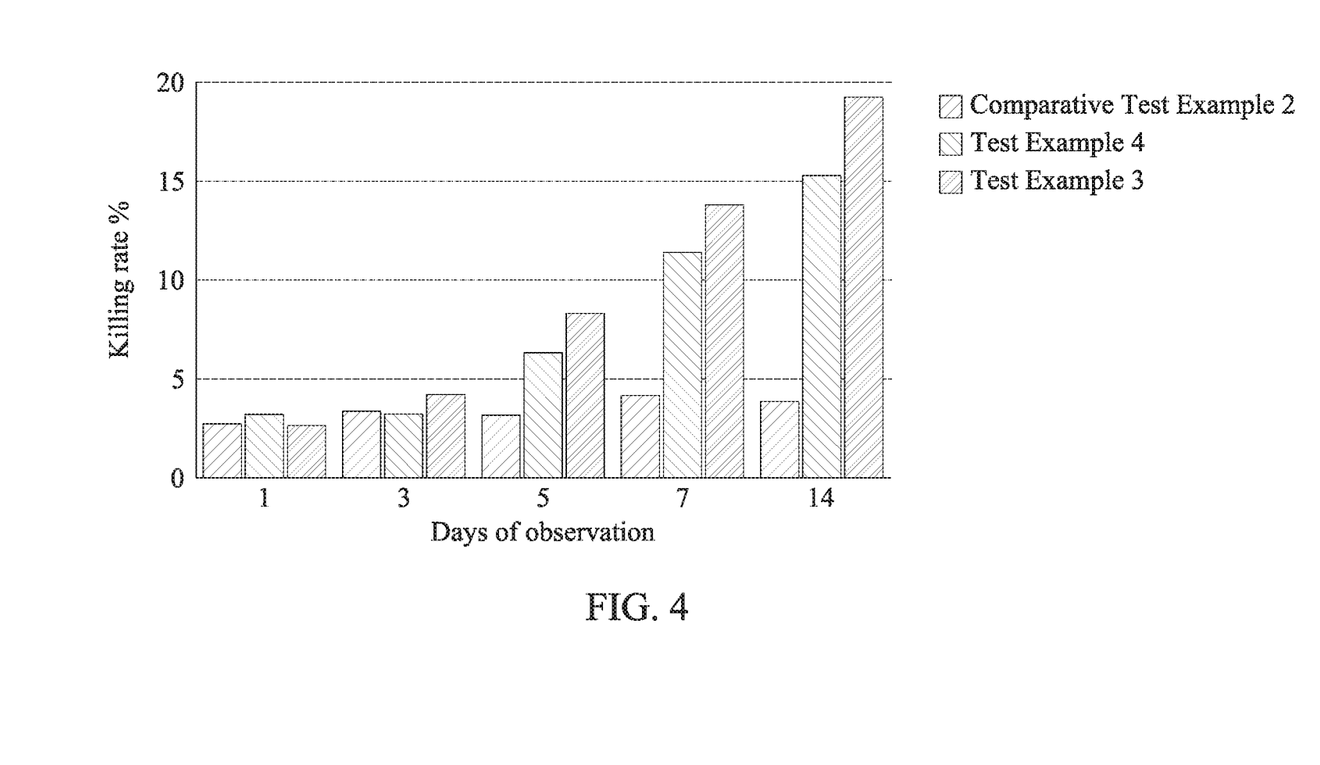
FIG. 4 is a comparative graph showing an evaluation on the killing rate of mouse natural killer cells caused by mushroom β-glucan prepared by different preparation methods according to an embodiment of the present disclosure.

Tests were performed on 15 mice. The mushroom β-glucan of above Example 10 was re-dissolved in distilled deionized water to form a 60 mg/mL aqueous solution of mushroom β-glucan, the mushroom β-glucan solution is fed to mice at a dose of 0.5 mL/day, equaling to each mouse uptaking about 30 mg of mushroom β-glucan per day. Spleens of mice were taken at days 1, 3, 5, 7 and 14 respectively, natural killer cells are isolated and their killing abilities are detected, number of cells having killing abilities per 100 cells was calculated, and the results are shown in FIG. 4.

Test Example 4: Test on Ability of Natural Killer Cells

The treatment method in Experimental Example 4 was the same as that in Experimental Example 3. However, direct extraction with ethanol was performed on the mushroom β-glucan in place of the ultrasonic rupturing technique. Their effects on the killing ability of natural killer cells were evaluated, and the results are shown in FIG. 4.

Comparative Test Example 2: Test on Ability of Natural Killer Cells

The treatment method in Comparative Experimental Example 2 was the same as that in Experimental Example 3. However, physiological saline was used in place of the mushroom β-glucan solution for feeding mice. Evaluations on its effect on killing ability of natural killer cells were performed, and the results are shown in FIG. 4.

As shown in FIG. 4, the killing rates of natural killer cells in mice fed with mushroom β-glucan prepared by ultrasonic rupturing were higher than those in Comparative Test Example 2, and the killing rates of natural killer cells in mice fed with mushroom β-glucan prepared by ultrasonic rupturing were better than those in mice fed with the mushroom β-glucan extracted with ethanol.

Test Example 5: Preparation of Mushroom β-Glucan Powder

A composite was formed by using the mushroom β-glucan of Example 10 above and lactose added as an excipient (with the weight ratio of the β-glucan to lactose of 1:1), and was treated by freeze drying to obtain mushroom β-glucan powder. Evaluations on content of mushroom β-glucan in the mushroom β-glucan powder were performed, and the results are shown in Table 4.

Test Examples 6-10: Preparation of Mushroom β-Glucan Powder

The treatment methods in Experimental Examples 6-10 are the same as that in Experimental Example 5. However, changes to the excipients and drying modes are shown in Table 4. Evaluations on the contents of mushroom β-glucan in the mushroom β-glucan powder were performed by using the β-Glucanase Assay Kit manufactured by Megazyme Inc.

TABLE 4

| | Drying mode | excipient | Content of the mushroom β-glucan (%) |
|---|---|---|---|
| Experimental Example 5 | freeze drying | lactose | 20-40 |
| Experimental Example 6 | | starch | 40-50 |
| Experimental Example 7 | | Fibersol-2 | 45-60 |
| Experimental Example 8 | spray drying | lactose | 28-43 |
| Experimental Example 9 | | starch | 42-65 |
| Experimental Example 10 | | Fibersol-2 | 70-85 |

Test Example 11: Test of Water Content of the Mushroom β-Glucan Powder

A composite was formed by using the mushroom β-glucan of Example 14 above and Fibersol-2 added as an excipient (with the weight ratio of the β-glucan to Fibersol-2 of 2:1), and was treated by spray drying to obtain mushroom β-glucan powder. Evaluations on the water content of the mushroom β-glucan powder were performed, and the results are shown in Table 5.

Test Examples 12-30: Test of Water Content of the Mushroom β-Glucan Powder

The treatment methods in Experimental Examples 12-30 were the same as that in Experimental Example 11. However, changes utilization examples of β-glucan and the weight ratio of β-glucan to excipient are shown in Table 5. Evaluations on the water content of the mushroom β-glucan powders were performed.

TABLE 5

| | Weight ratio of the β-glucan to the excipient | Application examples of the β-glucan | Species of the mushroom | Water content of the mushroom β-glucan powder (%) |
|---|---|---|---|---|
| Experimental Example 11 | 2:1 | Example 14 | Schizophyllum commue | 4.92 |
| Experimental Example 12 | | Example 13 | Ganoderma lucidum | 4.86 |

TABLE 5-continued

| | Weight ratio of the β-glucan to the excipient | Application examples of β-glucan | Species of the mushroom | Water content of the mushroom β-glucan powder (%) |
|---|---|---|---|---|
| Experimental Example 13 | | Example 15 | Antrodia cinnamomea | 4.25 |
| Experimental Example 14 | | Example 21 | Coriolus versicolor | 4.33 |
| Experimental Example 15 | 1:1 | Example 14 | Schizophyllum commue | 4.85 |
| Experimental Example 16 | | Example 13 | Ganoderma lucidum | 4.74 |
| Experimental Example 17 | | Example 15 | Antrodia cinnamomea | 4.32 |
| Experimental Example 18 | | Example 21 | Coriolus versicolor | 4.26 |
| Experimental Example 19 | 1:2 | Example 14 | Schizophyllum commue | 4.57 |
| Experimental Example 20 | | Example 13 | Ganoderma lucidum | 4.46 |
| Experimental Example 21 | | Example 15 | Antrodia cinnamomea | 4.25 |
| Experimental Example 22 | | Example 21 | Coriolus versicolor | 4.23 |
| Experimental Example 23 | 1:3 | Example 14 | Schizophyllum commue | 4.33 |
| Experimental Example 24 | | Example 13 | Ganoderma lucidum | 4.31 |
| Experimental Example 25 | | Example 15 | Antrodia cinnamomea | 4.21 |
| Experimental Example 26 | | Example 21 | Coriolus versicolor | 4.23 |
| Experimental Example 27 | 1:5 | Example 14 | Schizophyllum commue | 4.29 |
| Experimental Example 28 | | Example 13 | Ganoderma lucidum | 4.27 |
| Experimental Example 29 | | Example 15 | Antrodia cinnamomea | 4.22 |
| Experimental Example 30 | | Example 21 | Coriolus versicolor | 4.24 |

As seen in Table 5, the products of mushroom β-glucan powder after spray drying treatment contain water of 5.0% or less, which meets the current requirement on powdery raw materials in most food processing industries.

Test Example 31: Test on Solubility

Evaluation on solubility of the mushroom β-glucan powder was performed by using a 10 wt % solution of the mushroom β-glucan powder of Test Example 11 in water formulated at a temperature of 4° C., and the result is shown in Table 6.

Test Examples 32-43: Test on Water Solubility of the Mushroom β-Glucan Powder The treatment methods of Experimental Examples 32-43 were the same as that in Experimental Example 31. However, changes to the temperatures and the mushroom β-glucan powder used are shown in Table 6, and evaluations on the solubility of the mushroom β-glucan powder were performed.

TABLE 6

| | Temperature (° C.) | Application examples of the mushroom β-glucan powders | Species of the mushroom | Dissolution |
|---|---|---|---|---|
| Experimental Example 32 | 4 | Experimental Example 11 | Schizophyllum commue | ○ |
| Experimental Example 33 | | Experimental Example 12 | Ganoderma lucidum | ○ |
| Experimental Example 34 | | Experimental Example 13 | Antrodia cinnamomea | ○ |
| Experimental Example 35 | | Experimental Example 14 | Coriolus versicolor | ○ |
| Experimental Example 36 | 25 | Experimental Example 11 | Schizophyllum commue | ○ |
| Experimental Example 37 | | Experimental Example 12 | Ganoderma lucidum | ○ |
| Experimental Example 38 | | Experimental Example 13 | Antrodia cinnamomea | ○ |
| Experimental Example 39 | | Experimental Example 14 | Coriolus versicolor | ○ |
| Experimental Example 40 | 37 | Experimental Example 11 | Schizophyllum commue | ○ |
| Experimental Example 41 | | Experimental Example 12 | Ganoderma lucidum | ○ |
| Experimental Example 42 | | Experimental Example 13 | Antrodia cinnamomea | ○ |
| Experimental Example 43 | | Experimental Example 14 | Coriolus versicolor | ○ |

○: Dissolved completely;
X: Undissolved.

It can be seen from Table 6 that, since Fibersol-2 is water-soluble and the mushroom β-glucan of the present disclosure can also be dissolved in water well, the prepared highly pure mushroom β-glucan powder also has good water solubility.

The Examples described above are used for the purpose of illustration only, rather than limiting the present disclosure. Modifications and alternations can be done on the examples described above by any one skilled in the art without departing from the spirit and scope of the present disclosure. Therefore, the scope of the present disclosure is defined by the claims appended to the present disclosure, and it should be encompassed by the technical contents disclosed herein as long as the effects and purposes of the present disclosure are not influenced.

What is claimed is:

1. A method for preparing mushroom β-glucan, comprising:
   incubating mushroom mycelium in a liquid culture to increase yields of the mushroom mycelium and the mushroom β-glucan, wherein the liquid culture comprises at least two ingredients selected from the group consisting of glucose, trehalose, dietary fiber, mannose and a derivative thereof;
   rupturing the mushroom mycelium in the liquid culture with a continuous multiple-ultrasonic equipment in a plurality of rupturing tanks arranged in a sequence; and
   removing insoluble matters from the liquid culture,
   wherein ultrasonic frequencies employed in each of the rupturing tanks are in a range from 20 kHz to 70 kHz and the ultrasonic frequencies employed in the rupturing tanks are different from one another.

2. The method of claim 1, wherein the mushroom mycelium is of a mushroom selected from the group consisting of Schizophyllum commune, Agaricus blazei, Cordyceps sinensis, Ganoderma lucidum, Coriolus versicolor, Antrodia

*camphorata, Phellinus linteus, Pleurotus citrinopileatus, Lentinula edodes, Hericium erinaceus, Auricularia auricula* and *Flammulina velutipes*.

3. The method of claim 1, wherein the liquid culture comprises glucose, trehalose and mannose at a weight ratio of 5:1:1 to 1:1:1, or the liquid culture comprises glucose, trehalose and mannitol at a weight ratio of 5:1:1 to 1:1:1.

4. The method of claim 1, wherein the dietary fiber is dextrin.

5. The method of claim 4, wherein the dextrin is indigestible dextrin, and the liquid culture comprises indigestible dextrin, glucose, trehalose and mannose at a weight ratio of 1:1:1:1 to 1:10:10:10.

6. The method of claim 1, wherein the liquid culture further comprises at least one microelement selected from the group consisting of vitamin A, vitamin B1, vitamin B2, vitamin B12, vitamin C, vitamin D, folic acid, calcium, magnesium, phosphorus and iron.

7. The method of claim 1, wherein the mushroom mycelium in the liquid culture is ruptured with the continuous multiple-ultrasonic equipment at a temperature of 2° C. to 18° C.

8. The method of claim 1, wherein the mushroom mycelium in the liquid culture is ruptured with the continuous multiple-ultrasonic equipment in at least three rupturing tanks arranged in a sequence, and the ultrasonic frequencies employed in the at least three rupturing tanks are 20 kHz to 30 kHz, 35 kHz to 45 kHz and 55 kHz to 65 kHz, respectively.

* * * * *